(12) United States Patent (10) Patent No.: US 8,146,444 B2
Shin (45) Date of Patent: Apr. 3, 2012

(54) ULTRA FILTRATION SYSTEM FOR ON-LINE ANALYZER

(76) Inventor: Yun ho Shin, Gyeonggi-do (KR)

( * ) Notice: Subject to any disclaimer, the term of this patent is extended or adjusted under 35 U.S.C. 154(b) by 771 days.

(21) Appl. No.: 12/297,180

(22) PCT Filed: Mar. 16, 2007

(86) PCT No.: PCT/KR2007/001302
§ 371 (c)(1),
(2), (4) Date: Oct. 14, 2008

(87) PCT Pub. No.: WO2007/119928
PCT Pub. Date: Oct. 25, 2007

(65) Prior Publication Data
US 2009/0165576 A1 Jul. 2, 2009

(30) Foreign Application Priority Data
Apr. 14, 2006 (KR) .................. 10-2006-0034151

(51) Int. Cl.
*G01N 1/10* (2006.01)
(52) U.S. Cl. ..................... 73/863.23; 210/650
(58) Field of Classification Search ............... 73/863.21, 73/863.23, 863.24; 210/650
See application file for complete search history.

(56) References Cited

U.S. PATENT DOCUMENTS

| | | |
|---|---|---|
| 6,324,898 B1 | 12/2001 | Cote et al. |
| 2003/0150807 A1 | 8/2003 | Bartels et al. |
| 2009/0151355 A1* | 6/2009 | Fujie et al. ............. 60/657 |
| 2010/0159524 A1* | 6/2010 | Smith et al. ............. 435/91.1 |

FOREIGN PATENT DOCUMENTS

| | | |
|---|---|---|
| JP | 63-051907 | 3/1988 |
| JP | 63-097203 | 4/1988 |
| KR | 20020062248 | 7/2002 |

OTHER PUBLICATIONS

International Search Report for PCT/KR2007/001302, mailed Jun. 28, 2007.

* cited by examiner

*Primary Examiner* — Hezron E Williams
*Assistant Examiner* — Nashmiya Fayyaz
(74) *Attorney, Agent, or Firm* — Nixon & Vanderhye P.C.

(57) ABSTRACT

The present invention relates to a system for pretreating a test sample in order to analyze a test sample containing suspended solids in an on-line analyzer can, and more particularly to an ultra filtration system for an on-line analyzer for filtering suspended solids in order to stably quantitatively analyze a test sample containing a large amount of suspended solids using a module-type hollow fiber membrane filter intake system in an online analyzer. The ultra filtration system according to the present invention may be useful to obtain a reliable analysis result of a test sample using a filtered water in the field of environments, foods, chemistry, microorganisms, etc. by continuously separating solids from a liquid test sample containing a large amount of the solids and optimizing the test sample, in order to analyze the test sample in an on-line analyzer, and also to sense and swiftly respond to the real-time change in process and to minimize unnecessary manpower wastes, for example, extending a life span of an on-line analyzer, and maintaining, examining and correcting the analyzer, etc.

4 Claims, 7 Drawing Sheets

ULTRA FILTRATION SYSTEM FOR ON-LINE ANALYZER

This application is a U.S. national phase of International Application No. PCT/KR2007/001302, filed 16 Mar. 2007, which designated the U.S. and claims priority to Application No. KR 10-2006-0034151, filed 14 Apr. 2006; the entire contents of each of which are hereby incorporated by reference.

TECHNICAL FIELD

The present invention relates to a system for pretreating a test sample in order to analyze a test sample containing suspended solids in the on-line analyzer, and more particularly to an ultra filtration system for an on-line analyzer for filtering suspended solids in order to stably quantitatively analyze a test sample containing a large amount of suspended solids using a module-type hollow fiber membrane filter intake system.

BACKGROUND ART

Generally, an on-line analyzer is used for analyzing the components of various waters such as household water, residential water, etc., and determines whether it is suitable to be used for water. In the case of the household water, the on-line analyzer is, for example, used to determine whether the household water can be used for drinking water or residential water, or to determine whether the industrial waste water or discharged water discharged from a cattle shed and the like is suitable for the discharged water standard for protecting the environments.

However, when the on-line analyzer is used for measuring the residential water or waste water containing a large amount of suspended solids without pretreatment such as filtering, a path of the on-line analyzer may be clogged by the solid substance, or a normal operation of a valve installed in the path of the on-line analyzer is hampered by the solids, which causes a serious obstacle to the measurement. And furthermore, it is difficult to exactly analyze the water, because a thin film is formed on the installed electrode, thereby resulting in poor reliability in analysis.

In order to solve the above problems in the art, Korean Patent Publication No. 2006-0029126 discloses a pre-treatment device of suspended solid attached submerged reactor for eliminating the suspended solid contained in the samples to be analyzed, in which an interchanging term of the filter can be extended by simplifying the construction of installation and separation of the filter.

However, when the raw water containing a large amount of suspended solids is filtered for a long time, it is impossible to separate or remove the solids adhered to the filter, except an interchanging method of the filter. Therefore, the time loss and maintenance cost may be increased due to the interchange of the filter.

As another published invention, Korean Patent Publication No. 2006-0013824 discloses a device of preprocessing for use in apparatus for measuring contaminated substance, in which the device includes a grinder for grinding the suspended solids, of which the grinder is rotated by means of driving of a motor in an operation room (a chamber) having a filter installed inside.

However, such a device may extend an interchanging term of the filter for a little while, but it did not propose no means for removing solids adhered to the filter. Therefore, problems on the required time and maintenance cost for interchanging the filter remains to be solved.

DISCLOSURE OF THE INVENTION

Technical Problem

The object of the present invention is to provide an ultra filtration system for an on-line analyzer capable of obtaining an exact analysis data by filtering a test sample containing suspended solids and analyzing the filtered test sample.

Another object of the present invention is to provide an ultra filtration system for an on-line analyzer capable of cleaning a filter by inversely pressurizing a filtered water into a hollow fiber in order to effectively remove suspended solids adhered to the filter, or of preventing solids and floated substance from being accumulated in a bottom of a housing or being attached to a surface of a hollow fiber filter, that is, of cleaning a filter by blowing the air into a lower portion of a hollow fiber module inside the housing.

Technical Solution

In order to accomplish the above object, the present invention provides an ultra filtration system for an on-line analyzer for purifying and analyzing a test sample containing the suspended substance, the ultra filtration system comprising:

a hollow fiber module having a hollow fiber filter inside a housing, hollow fiber filter being connected to an upper tank and the lower tank respectively;

the first pipe having one end connected to a first pump submerged in a raw water test sample and the other end connected to a lower portion of the housing and including the first valve;

the second pipe connected to an upper portion of the housing;

the third pipe connected to the upper portion of the housing and including the third valve;

the pipe having one end connected to the lower portion of the housing and the other end connected to the second pipe and including the second valve;

the fourth pipe divided and connected with the fifth pipe and the ninth pipe, the fifth pipe having one end connected to the upper or lower tank and the other end respectively connected to the fourth three way valve, and the ninth pipe being connected to the fifth three way valve;

the sixth pipe having one end connected to the fourth three way valve and the other end connected to the fifth three way valve, and including the second pump and the flowmeter;

the seventh pipe having one end connected to the fifth three way valve and the other end connected to a test sample collection tank;

the eighth pipe having one end connected to the fourth three way valve and a bottom of the test sample collection tank and the other end connected to an analyzer, and including a third pump; and the tenth pipe connected to the test sample collection tank to overflow a test sample.

Here, the present invention is characterized in that the ultra filtration system comprises:

the cylindrical shape—housing having a hollow fiber module;

upper/lower tanks formed in inside upper/lower portions of the housing; and the hollow fiber filter having the form of a plurality of pipes passed through the upper/lower tanks and having a plurality of filter holes formed in its surface.

According to the above characteristics, it is possible to can suck in the raw water test sample with the first pump, to filter solids through the hollow fiber module to obtain the filtrate sample, to measure the filtrate sample by the analyzer, and also possible to clean the filter mesh by operating the second pump to inversely pressurize the filtered water stored in a test sample collection tank.

Also, the ultra filtration system of the present invention is characterized in that the hollow fiber module of the present invention further includes:

the diffuser pipe having the form of pipes passed through the center of the upper or lower tanks, and having at least one air ventilation hole formed in its lower portion; and the supply pipe having one end connected to the bottom of the diffuser pipe and the other end connected to the air pressure pump.

According to the above characteristics, the ultra filtration system of the present invention can clean a hollow fiber filter by operating an air pressure pump to blow air into a diffuser pipe under the pressure.

Effects of the Invention

According to the present invention, it is possible to obtain the reliable analysis result of a test sample using the filtered water in the field of environments, foods, chemistry, microorganisms, etc. by continuously separating solids from a liquid test sample containing a large amount of the solids and optimizing the test sample for analyzing the test sample in the on-line analyzer.

The ultra filtration system according to the present invention may be useful to filter suspended solids through the filter, and also to obtain a constant amount of a test sample for on-line analysis continuously by inversely pressurizing the filtered water into the hollow filter to clean a hollow fiber filter, or by cleaning the filter clogged when it is used for a long time by blowing the air into a lower portion of the hollow fiber module inside the housing to prevent solids and floated substance from being accumulated in the bottom of the housing or from being adhered to the surface of the hollow fiber filter.

Also, the ultra filtration system according to the present invention may be useful to respond swiftly to the change in process such as reduction in filtering efficiency by sensing the flow rate of the filtered water in a real-time manner, and minimize unnecessary manpower wastes, for example, extending the durability of the on-line analyzer, and maintaining, examining and correcting the analyzer, etc.

BRIEF DESCRIPTION OF THE DRAWINGS

These and other features, aspects, and advantages of preferred embodiments of the present invention will be more fully described in the following detailed description, taken accompanying drawings. In the drawings.

BEST MODE FOR CARRYING OUT THE INVENTION

Hereinafter, preferred embodiments of the present invention will be described in detail referring to the accompanying drawings. Prior to the description, it should be understood that the terms used in the specification and appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just a preferable example for the purpose of illustrations only, not intended to limit the scope of the invention, so it should be understood that other equivalents and modifications could be made thereto without departing from the spirit and scope of the invention.

The present invention relates to a system for pretreating a test sample for analyzing a test sample containing suspended solids in an on-line analyzer, and more particularly to an ultra filtration system for an on-line analyzer for filtering suspended solids, in order to analyzing stably quantitatively a test sample containing a large amount of suspended solids in an on-line analyzer using a module-type hollow fiber membrane filter intake system.

In order to easily understand the preferred embodiments of the present invention in more detail, a configuration of the system of the present invention, and suspended solids and a hollow fiber filter will be explained with reference to FIG. 1.

Figure 1:
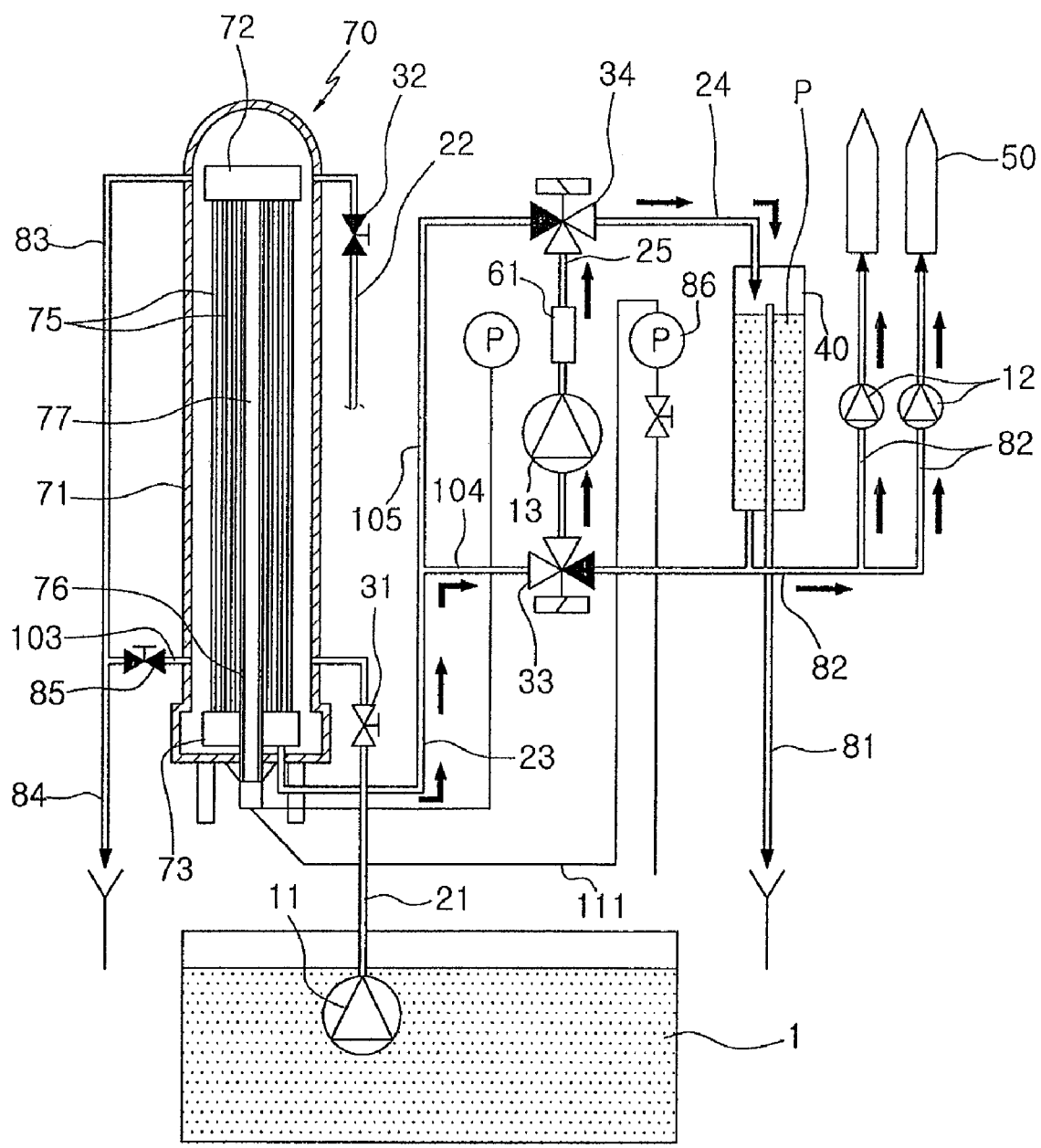
FIG. 1 is a systematic view showing the full configuration and an operation of the filtration system according to the present invention.
Figure 4:
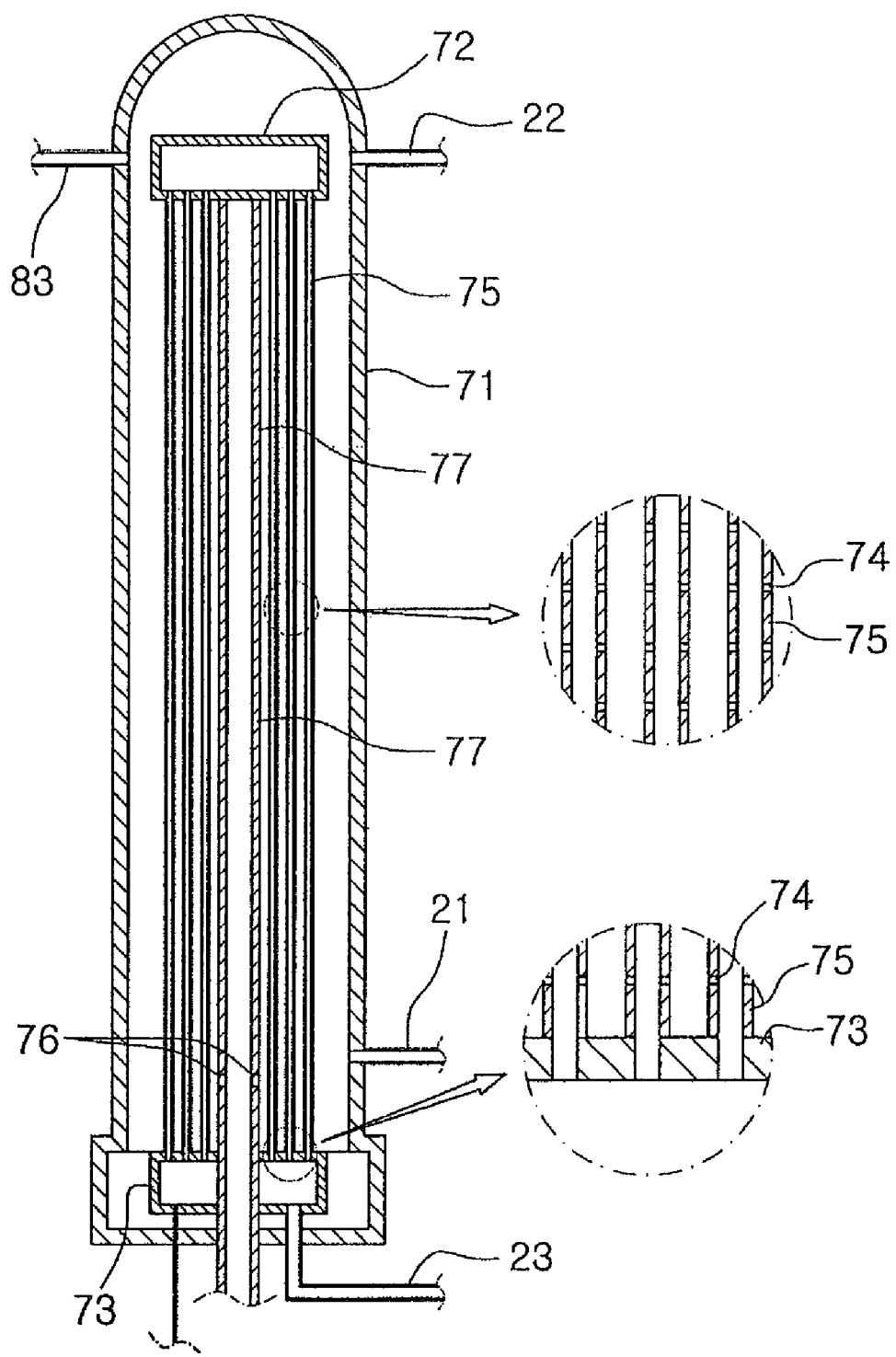
FIG. 4 is a cross-sectional view showing an inner configuration of a hollow fiber filter in the filtration system according to the present invention.

Referring to FIG. 1 and FIG. 4, the system of the present invention for purifying and analyzing a test sample containing suspended solids includes a hollow fiber filter 75 inside a housing 71, and an upper or lower portion of the hollow fiber filter includes a hollow fiber module 70 connected to the upper tank 72 and the lower tank 73.

The housing 71 has a cylindrical shape in the hollow fiber module 70, and the upper/lower tanks 72, 73 are formed respectively on inside upper/lower portions of the housing 71, and the hollow fiber filter 75 has the form of a plurality of pipes passed through each of the upper/lower tanks 72, 73.

Of course, a plurality of filter holes 74 are formed on a surface of the hollow fiber filter 75 for the purpose of a filtering operation, and a test sample (P) for analysis filtered through the filter holes 74 is the most optimized for an analyzer 50 to measure components of the test sample (P).

The first pipe 21 is a path for transferring a raw water test sample 1 into a housing 71, and it has one end connected to the first pump 11 submerged in the raw water test sample 1 and the other end connected to the lower portion of the housing 71, and includes the first valve 31 for controlling switching of the raw water test sample in a duck.

The second pipe 83 is connected to the upper portion of the housing 71 to serve to overflow the raw water test sample 1 flowing in the housing 71.

The third pipe 22 is connected to the upper portion of the housing 71 and includes the third valve 32 formed on its duck, and a pipe 103 has one end connected to the lower portion of the housing 71 and the other end connected to the second pipe 83 and includes the second valve 85 formed on its duck. Here, the third pipe 22 and the pipe 103 take main part in washing the inside of the housing 71.

That is to say, the second valve 85 and the third valve 32 are usually closed, but a washing water such as a running water is supplied into the housing 71 when the third valve 32 is open if the inside of the hollow fiber module 70 should be cleaned or if necessary.

At this time, if the second valve 85 of the pipe 103 connected to the lower portion of the housing 71 is open together with the second pipe 83 having an overflowing function of the hollow fiber module 70, the washing water introduced into the housing 71, raw water test sample 1 containing a test sample for analysis or suspended solids, etc. are more swiftly discharged off through the pipe 103, and therefore no residues are present in the housing 71.

The fourth pipe 23 is divided and connected to the fifth pipe 104 and the ninth pipe 105, the fifth pipe 104 having one end connected to a lower tank 73 and the other end connected to the fourth three way valve 33, and the ninth pipe 105 being connected to the fifth three way valve 34. Here, the fourth pipe 23 is a duck for transferring a test sample (P) for analysis, which is filtered in the housing 71, to a test sample collection tank 40, or inversely transferring a test sample.

The sixth pipe 25 has one end connected to the fourth three way valve 33 and the other end connected to the fifth three way valve 34, and includes a second pump 13 and a flowmeter 61 formed on its duck.

The seventh pipe 24 has one end connected to the fifth three way valve 34 and the other end connected to the test sample collection tank 40, and therefore injects the test sample (P) for analysis into the test sample collection tank 40.

The eighth pipe 82 has one end connected respectively to the fourth three way valve 33 and a lower portion of the test sample collection tank 40 and the other end connected to an analyzer 50, and includes a third pump 12 formed on its duck. At this time, the test sample (P) for analysis in the test sample collection tank 40 is transferred to the analyzer 50 by means of operation of the third pump 12.

The tenth pipe 81 is connected to the upper portion of the test sample collection tank 40 to overflow the test sample (P) for analysis, and therefore the test sample (P) for analysis stored in the test sample collection tank 40 is always maintained at a constant level.

Meanwhile, a tubular diffuser pipe 77 passed through the center of the upper/lower tanks 72, 73 has at least one air ventilation hole 76 formed on its lower portions, and the supply pipe 111 has one end connected to the lower portion of the diffuser pipe 77 and the other end connected to an air pressure pump 86, as shown in FIG. 4.

An air pressure pump 86 serves to inject the air into the diffuser pipe 77 through the supply pipe 111.

In the present invention, the raw water test sample 1 contains solids that is not dissolved but suspended in water (hereinafter, referred to as 'solids.'), and floated substance are present in a floating state, a colloidal state or a dissolved state, depending on its particle size. Here, the floated substance have a particle diameter of 0.1 μm or more, the colloidal matters have a particle diameter of 0.1-0.001 μm, and the dissolved matters have a particle diameter of 0.001 μm or less.

Here a group belonging to the floated substance (SS: Suspended Solids) refers to particles having a diameter of 0.1 μm or more and colloid particles having a diameter of 0.01 μm or more, and such floated substance should be previously separated before they are examined and measured with an analyzer to ensure accuracy in examination and measurement of the floated substance.

Accordingly, the ultra filtration system of the present invention preferably selects a filter hole 74 to filter the floated substance having a particle size of 0.01 to 0.6 μm or more, and more preferably matters having a particle size of 0.1 μm or more in the substance dissolved or dispersed in a liquid solution, the filter hole 74 having pores having a diameter of 0.01 to 0.6 μm according to property of the raw water test sample 1 which is a subject to be tested.

A hollow fiber filter 75 is a tubular filter whose inner part is hollow, as its name. Here, low molecular weight substance (K, Mg, Ca, Na, Cl, etc.) in the raw water test sample 1 may be transmitted between the filters, and high molecular weight substance (floated substance (SS), *E-coli*, virus, bacteria, bacterial vibrio strain, Rhodophyceae, milk powder, colloidal solution, pyrogen, etc.) in the raw water test sample 1 may be separated in the filters.

A hollow fiber module 70 has a form where several tens to several thousands of hollow fibers having an outer diameter of 3 mm or less are bundled using a semipermeable membrane and put into a pressure vessel.

In the filtration of the floated substance, a raw water containing floated substance is pressurized to flow in the housing 71, and only low molecular weight substance and water, which are smaller than a hollow fiber filter hole, are passed through a filter hole 74 while the introduced raw water cross flows in a hollow fiber filter 75, and then penetrated into the hollow fiber. Then, the penetrated water flows in a lower tank 73 through the center of the hollow fiber, sucked in by means of a suction pressure of a second pump 13, and then collected in a test sample collection tank 40.

The hollow fiber filter 75 has an excellent filtering efficiency since it has a large area of a treatment membrane per unit volume, and also can clean a test sample in an inverse direction since it has self-supportability. Therefore, a membrane surface may be easily cleaned even if it is contaminated, and it is possible to swiftly recover a filtering performance after the cleaning.

According to the present invention, an on-line analyzer may be operated under the best conditions since a constant amount of a test sample for analysis may be continuously prepared by periodically cleaning a filter for the test sample being easily contaminated in general.

EXAMPLES

The present invention will next be described in detail by way of examples, which should not be construed as limiting the invention.

Hereinafter, in the system according to the present invention, at first, a procedure in which a raw water test sample is changed into a test sample for analysis (a filtered water) and analyzed using an on-line analyzer will be described, and in second, a procedure in which a hollow fiber module is cleaned with the test sample for analyzer will be described, and in third, a procedure in which the hollow fiber filter is shaken off with the air will be described.

In the accompanying drawings, a valve marked with a black color means that the valve remains being closed, and an unmarked valve means that the valve remains open. Then, a configuration of the system according to the present invention will be more clearly understood through the description about an operation of the system.

At first, the step of filtering a raw water test sample 1 containing a large amount of solids is described.

Referring to FIG. 1, the raw water test sample 1 is pumped by means of operation of a first pump 11 to flow in the first pipe 21, and then flows in a hollow fiber module 70 and collected in an upper tank 72 or a lower tank 73, while filtering floated substance using a hollow fiber filter 75.

The filtered test sample (P) for analysis flows in a fourth pipe 23 by means of operation of a second pump 13 and arrives at a fourth three way valve 33 via a fifth pipe 104. At this time, the test sample (P) for analysis enters a sixth pipe 25 provided with a flowmeter 61 by means of the continuous pumping operation of the second pump 13 since the fourth three way valve toward an eighth pipe 82 remains closed, and then the flowmeter 61 is indicated so that it can measure a flow rate of the filtered test sample (P) for analysis.

The test sample (P) for analysis passed through the sixth pipe 25 is injected into a test sample collection tank 40 for analysis through the fifth three way valve 34, the test sample collection tank 40 being provided in a head of a seventh pipe 24. Then, the test sample (P) stored in the test sample collection tank 40 is pumped by means of operation of the third pump 12 to flow in an on-line analyzer 50 through the eighth pipe 82, and then the on-line analyzer measures components of the collected raw water test sample.

Figure 5:
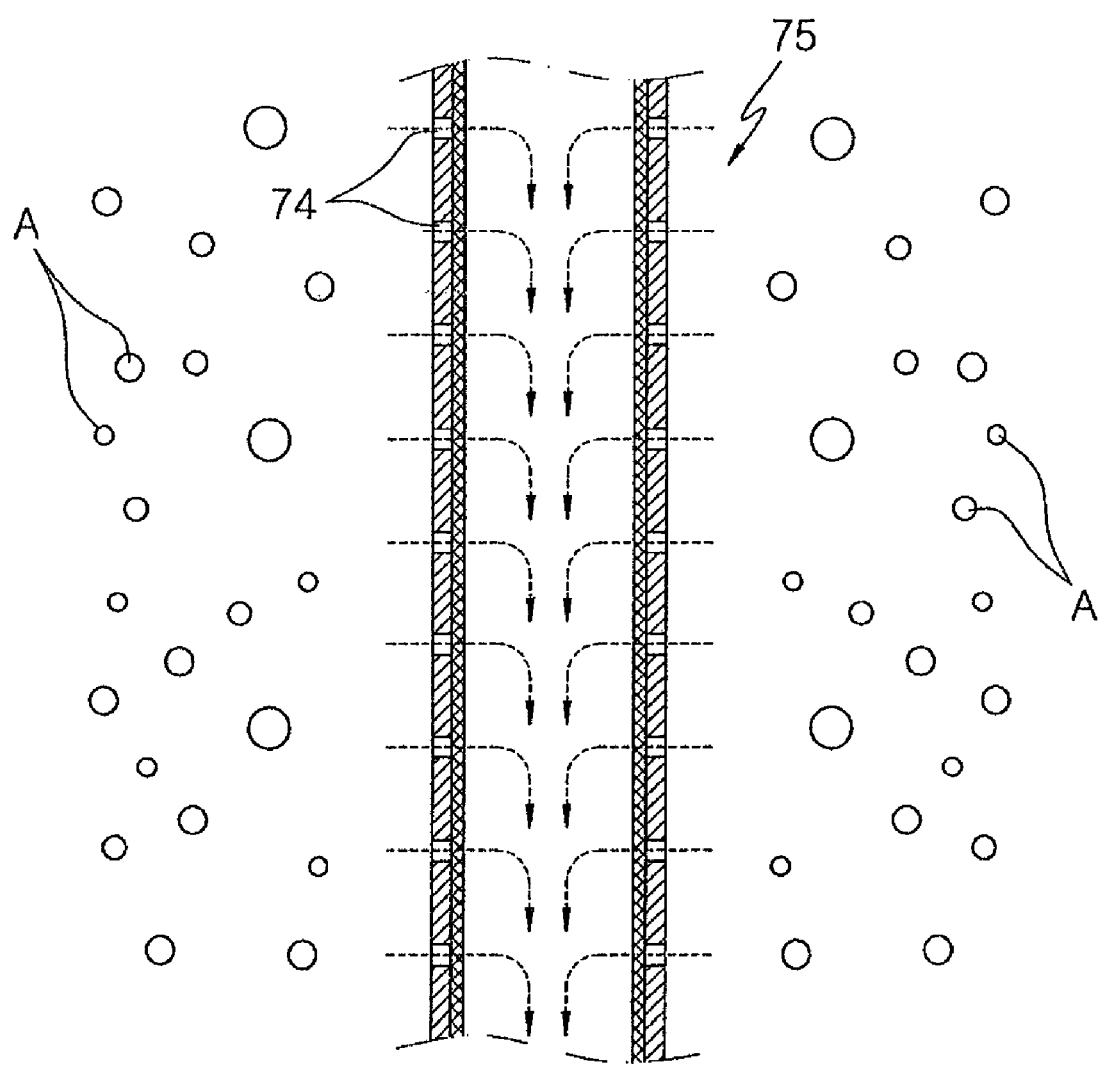
FIG. 5 is a cross-sectional view showing a filtering operation of a hollow fiber filter in the filtration system according to the present invention.

In the filtering operation of the hollow fiber filter 75 as shown in FIG. 1, the raw water test sample 1 flows inside the housing 71 through a first switching valve 31 which is opened by means of the pumping operation of the first pump 11, and the raw water test sample 1 continues to flows by means of the pumping operation of the first pump 11. Therefore, the raw water test sample 1 is penetrated into the hollow fiber filter 75 through each of the filter holes 74 of the hollow fiber filter 75, as shown in FIG. 4 and FIG. 5.

Of course, the floated substance having the larger diameter than the filter hole 74 is not penetrated through the filter holes 74, and remains in the housing 71. At this time, the floated substance remaining into the housing 71 overflows through the second pipe 83.

That is to say, the raw water test sample 1 continues to flows into the housing 71, and the unfiltered floated substance overflow with some of the raw water test sample through the second pipe 83 while being filtered through the hollow fiber filter 75.

The test sample (P) for analysis penetrated into a plurality of the hollow fiber filters 75 drop into a lower tank 73 by means of gravity, and the test sample (P) for analysis collected in the lower tank 73 is stored in the test sample collection tank 40 for analysis in the same manner as described above.

As shown in FIG. 5, the solids (A) having a certain particle size clogs the filter holes 74 of the hollow fiber filter 75 in the filtration of the hollow fiber filter 75, thereby resulting in reduced penetration efficiency of the raw water test sample. At this time, the penetration efficiency of the test sample can be determined by checking the fluctuation of a flow rate of the test sample (P) for analysis indicated in the flowmeter 61.

That is to say, if a flow rate indicator of the flowmeter 61 is lower than a set reference value, the filtering efficiency is proven to be low. At this time, the hollow fiber filter 75 should be necessarily cleaned.

Hereinafter, a cleaning operation of the hollow fiber module in the system of the present invention will be described.

Figure 2:
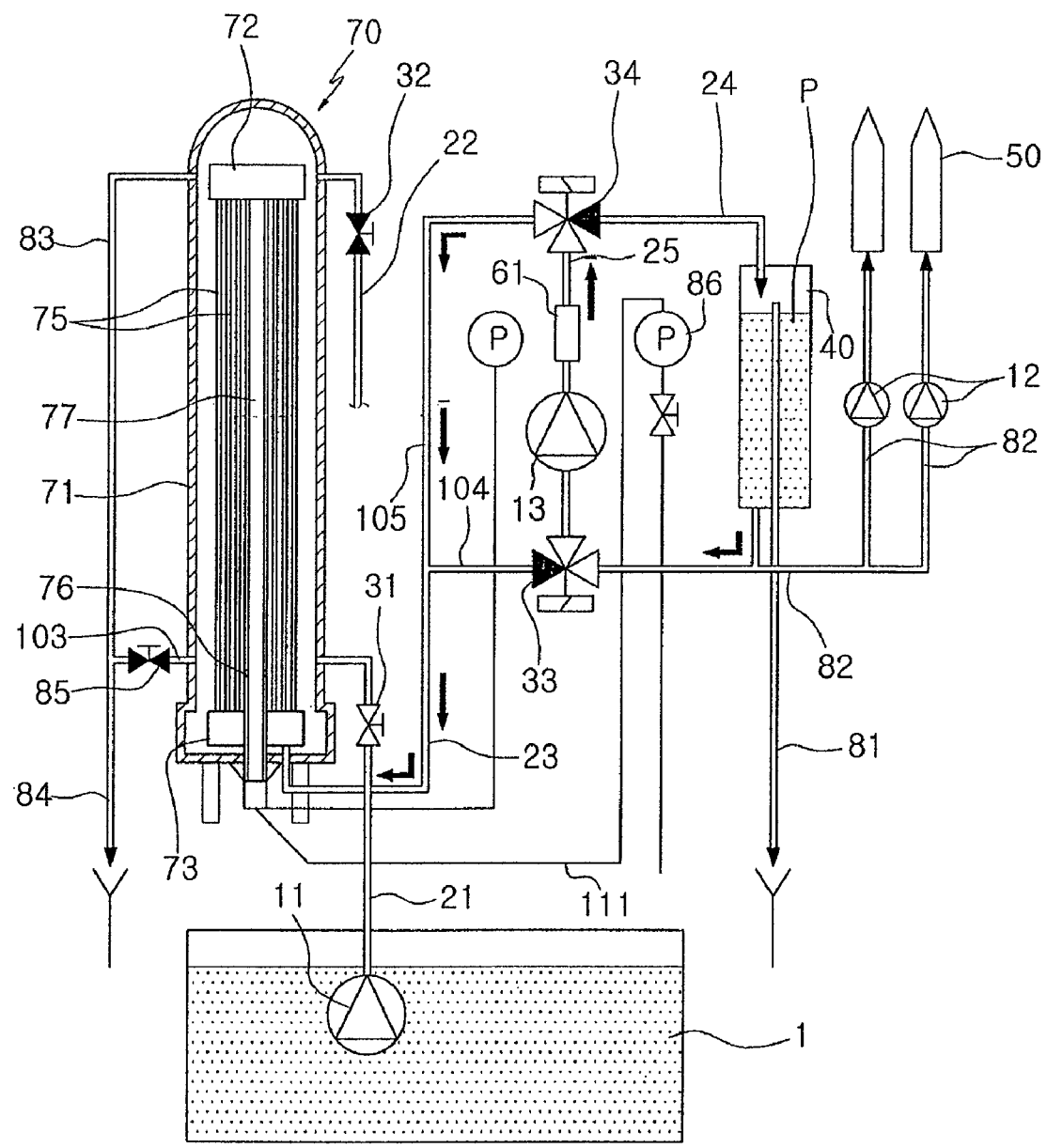
FIG. 2 is a systematic view showing the full configuration and an inverse transferring operation of a filtration system according to the present invention.
Figure 6:
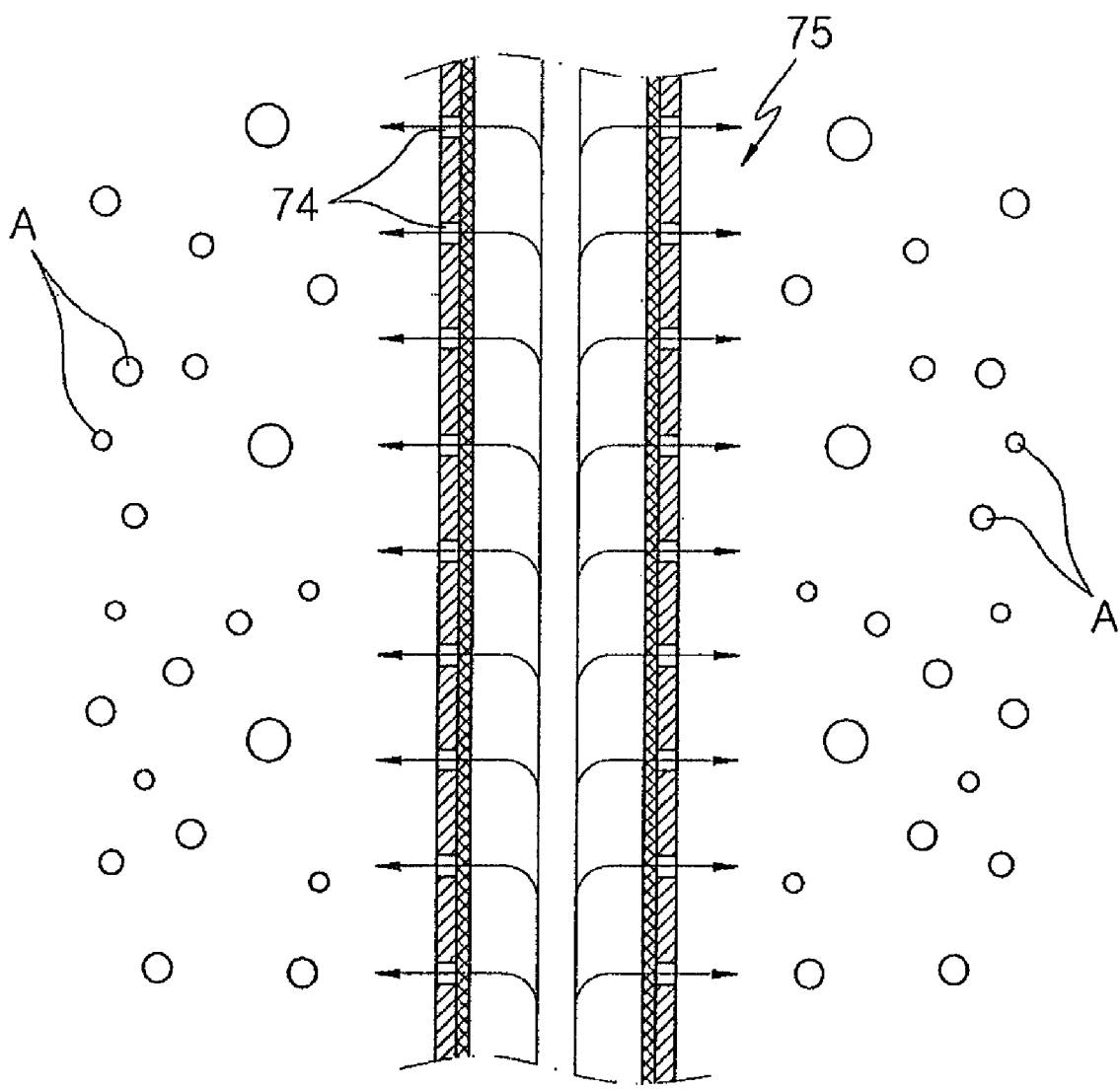
FIG. 6 is a cross-sectional view showing a cleaning operation of the hollow fiber filter by means of the inverse transfer in the filtration system according to the present invention.

As shown in FIG. 2 and FIG. 6, the test sample (P) for analysis stored in the test sample collection tank 40 overflows through the tenth pipe 81, and therefore a constant amount of the test sample (P) for analysis is stored in the test sample collection tank 40, and the hollow fiber filter 75 is cleaned with the test sample (P) for analysis stored in the test sample collection tank 40.

For the cleaning purpose, the connective portion of the fifth pipe 104 in the fourth three way valve 33 is firstly closed, the connective portion of the seventh pipe 24 in the fifth three way valve 34 is closed, and then the second pump 13 is operated.

If the second pump 13 is operated, the test sample (P) for analysis flows in through the eighth pipe 82, and sequentially flows into the housing 71 through the fourth pipe 23 via the sixth pipe 25 and the ninth pipe 105.

The test sample (P) for analysis flowing in the lower tank 73 in the housing 71 flows out into the outside of the hollow fiber filter 75, that is, the housing 71 via the filter hole 74 by means of the water pressure, as shown in FIG. 6. At this time, the test sample (P) for analysis is easily penetrated through the filter hole 74 since the solids (A) are already removed from the test sample (P) for analysis.

The solids (A) fit and adhered to the filter hole 74 are detached from the hollow fiber filter 75 during the cleaning operation, and then the test sample (P) for analysis containing the detached solids (A) overflows through the second pipe 83.

Figure 3:
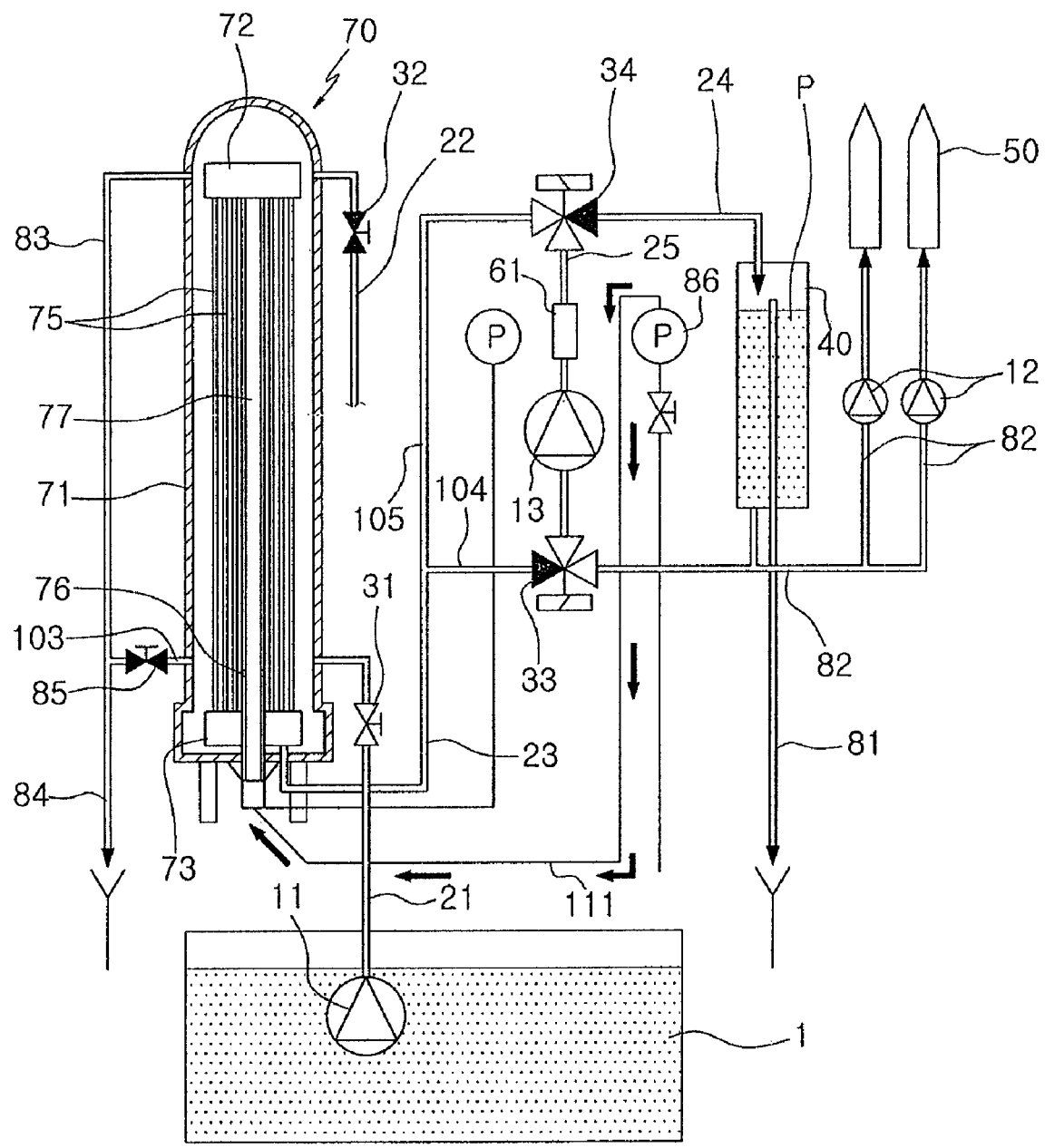
FIG. 3 is a systematic view showing the entire configuration and an air blowing operation of a filtration system according to the present invention.
Figure 7:
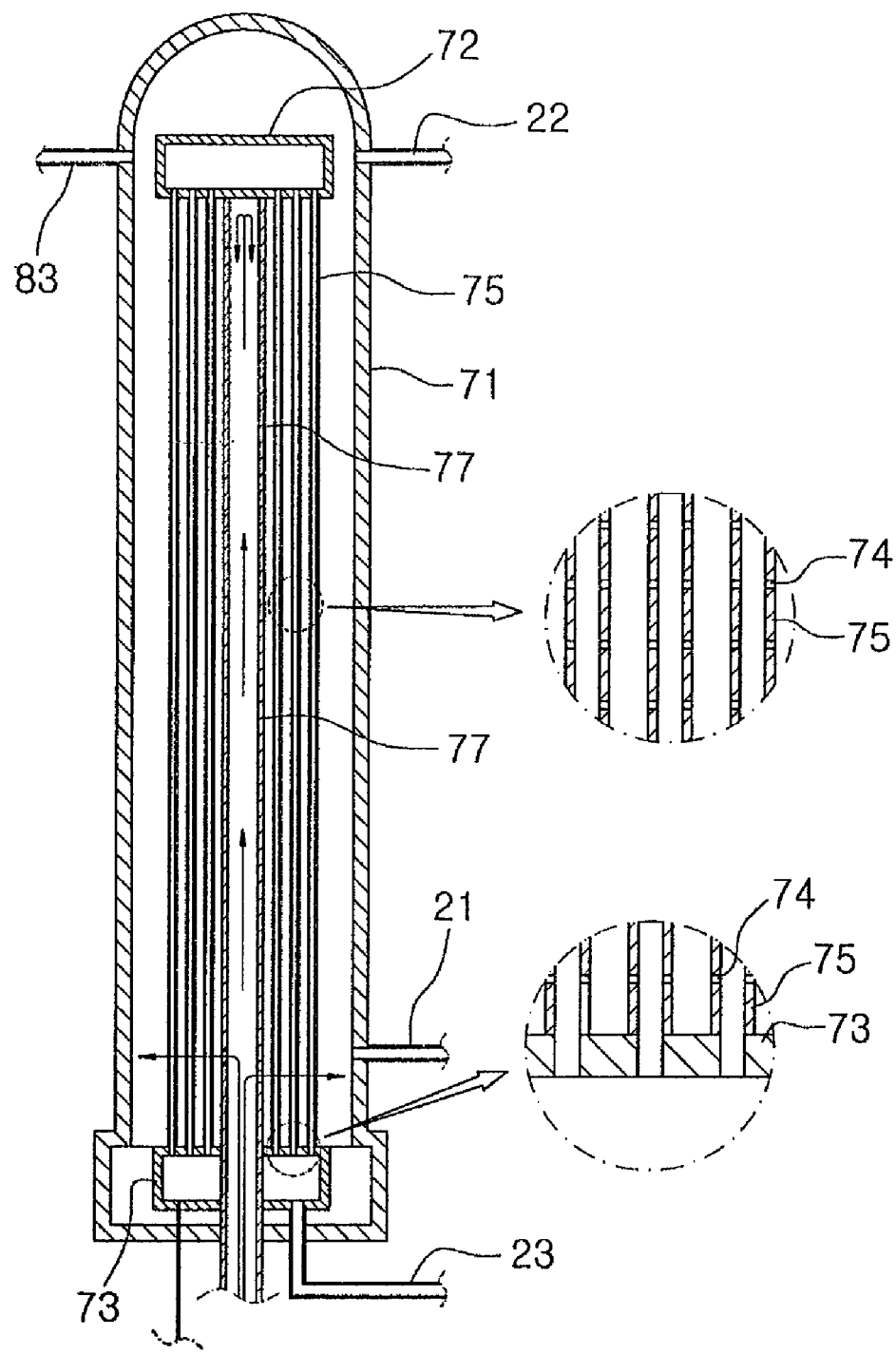
FIG. 7 is a cross-sectional view showing a cleaning operation of the hollow fiber filter by means of an air blowing process in the filtration system according to the present invention.

Meanwhile, according to the present invention, the hollow fiber filter 75 may be shaken off using the air, as shown in FIG. 3 and FIG. 7. Hereinafter, a cleaning operation of a filter using the air is described.

As described above, the supply pipe 111 installed with an air pressure pump 86 is connected to a lower portion of the diffuser pipe 77, and therefore if the air pressure pump 86 is operated, a compressed air generated in the air pressure pump 86 flows into the diffuser pipe 77 through the supply pipe 111.

The air flowing into the diffuser pipe 77 fiercely gusts out into air ventilation holes 76 formed in a lower portion of the diffuser pipe 77, and then the gusted air give pressure to a plurality of hollow fiber filters 75 arranged in the outside of the diffuser pipe 77 to cause vibrations. In this procedure, the solids (A) fit and adhered to the filter hole 74 are detached outside the hollow fiber filter 75.

That is to say, the solids (A) are detached due to the vibrations of the hollow fiber filter 75 by means of the air spraying, and the detached solids (A) floats inside the housing 71 by means of the air, and then overflows through the second pipe 83 along with the raw water test sample 1 flowing into the housing 71.

Also, washing water is injected into the housing 71 by closing the first switching valve 31 and opening the third valve 32, and then the washing water and the solids (A) may be more swiftly cleaned through the pipe 103 arranged in a lower portion of the housing 71 by opening the second valve 85 of the pipe 103.

According to the cleaning process, the hollow fiber module 70 may effectively filter the raw water test sample 1.

INDUSTRIAL APPLICABILITY

The ultra filtration system according to the present invention may be useful to obtain a reliable analysis result of a test sample using a filtered water in the field of environments, foods, chemistry, microorganisms, etc. by continuously separating solids from a liquid test sample containing a large amount of the solids and optimizing the test sample, in order to analyze the test sample in an on-line analyzer.

Also, the ultra filtration system according to the present invention may be useful to filter suspended solids through a filter, and also to obtain a constant amount of a test sample for on-line analysis at all time by inversely pressurizing a filtered water into a hollow fiber filter to clean a hollow fiber filter, or by cleaning a filter clogged when it is used for a long times by inversely transferring a filtered water or blowing the air in an opposite direction to clean a filter clogged when it is used for a long time.

Also, the ultra filtration system according to the present invention may be useful to sense a flow rate of a filtered water to respond swiftly to the real-time change in process such as reduction in filtering efficiency, and minimize unnecessary manpower wastes, for example, extending a life span of an on-line analyzer, and maintaining, examining and correcting the analyzer, etc.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. An ultra filtration system for an on-line analyzer for purifying and analyzing a test sample, the ultra filtration system comprising:
   a hollow fiber module having a hollow fiber filter inside a housing, the hollow fiber filter being connected to a lower tank;
   a first pipe having one end connected to a first pump submerged in a raw water test sample and another end connected to the housing's lower portion, and including a first valve;
   a second pipe connected to the housing's upper portion;
   a third pipe connected to the housing's upper portion, and including a third valve;
   a pipe having one end connected to the housing's lower portion and another end connected to the second pipe, and including a second valve;
   a fourth pipe divided and connected with a fifth pipe and a ninth pipe, the fifth pipe having one end connected to the lower tank and another end connected to a fourth valve, and the ninth pipe being connected to a fifth valve;
   a sixth pipe having one end connected to the fourth valve and another end connected to the fifth valve, and including a second pump and a flowmeter;
   a seventh pipe having one end connected to the fifth valve and another end connected to a test sample collection tank;
   a eighth pipe having one end connected to the fourth valve and the bottom of the test sample collection tank and another end connected to an analyzer, and including a third pump; and
   a tenth pipe connected to the test sample collection tank to overflow a test sample.

2. The ultra filtration system for an on-line analyzer according to claim 1, wherein in the hollow fiber module:
   the housing has a cylindrical shape;
   upper and lower tanks are formed, respectively, in inside upper and inside lower portions of the housing; and
   the hollow fiber filter has a plurality of pipes passed through the upper and the lower tanks, and a plurality of filter holes are formed in the filter's surface.

3. The ultra filtration system for an on-line analyzer according to claim 2, wherein the hollow fiber module further comprises:
   a diffuser pipe having pipes passed through the upper and the lower tanks' centers, and having at least one air ventilation hole formed in the housing's lower portion; and
   a supply pipe having one end connected to a bottom of the diffuser pipe and another end connected to an air pressure pump.

4. The ultra filtration system for an on-line analyzer according to claim 2, wherein a filter hole of the hollow fiber filter has a diameter of from 0.01 μm to 0.6 μm.

* * * * *